(12) United States Patent
Jung et al.

(10) Patent No.: US 10,497,483 B1
(45) Date of Patent: Dec. 3, 2019

(54) RADIATION SHIELD

(71) Applicants: Hanseo University Academic Cooperation Foundation, Seosan-si, Chungcheongnam-do (KR); Hong-Ryang Jung, Gwangmyeong-si (KR); Cheong-Hwan Lim, Suwon-si (KR); Ki-Jeong Kim, Gimpo-si (KR)

(72) Inventors: Hong-Ryang Jung, Gwangmyeong-si (KR); Cheong-Hwan Lim, Suwon-si (KR); Ki-Jeong Kim, Gimpo-si (KR)

(73) Assignees: HANSEO UNIVERSITY ACADEMIC COOPERATION FOUNDATION, Seosan-si, Chungcheongnam-Do (KR); Hong-Ryang Jung, Gwangmyeong-si, Gyeonggi-Do (KR); Cheong-Hwan Lim, Suwon-si, Gyeonggi-Do (KR); Ki-Jeong Kim, Gimpo-si, Gyeonggi-Do (KR)

( * ) Notice: Subject to any disclaimer, the term of this patent is extended or adjusted under 35 U.S.C. 154(b) by 0 days.

(21) Appl. No.: 16/242,290

(22) Filed: Jan. 8, 2019

(51) Int. Cl.
 *G21F 1/12* (2006.01)
 *A61B 6/10* (2006.01)

(52) U.S. Cl.
 CPC .............. *G21F 1/125* (2013.01); *A61B 6/107* (2013.01)

(58) Field of Classification Search
 CPC ... G21F 1/12; G21F 1/125; G21F 3/00; A61B 6/10; A61B 6/107
 See application file for complete search history.

(56) References Cited

U.S. PATENT DOCUMENTS

| 2007/0029513 A1* | 2/2007 | Treuth | G21F 3/02 |
| | | | 250/519.1 |
| 2011/0095209 A1* | 4/2011 | Cadwalader | A61B 6/107 |
| | | | 250/519.1 |
| 2014/0048730 A1* | 2/2014 | Niedzielski | A61B 6/107 |
| | | | 250/519.1 |

FOREIGN PATENT DOCUMENTS

| JP | 2010-279622 A | 12/2010 | |
| KR | 10-0909075 B1 | 7/2009 | |
| KR | 10-1527796 B1 | 6/2015 | |
| KR | 10-1607289 B1 | 3/2016 | |
| KR | 101607289 B1 * | 3/2016 | .............. A61B 6/10 |

* cited by examiner

*Primary Examiner* — David E Smith
(74) *Attorney, Agent, or Firm* — Saliwanchik, Lloyd & Eisenschenk

(57) ABSTRACT

Disclosed is a radiation shield for a radiotherapy apparatus including guide grooves formed at widthwise opposite ends of a bed in a lengthwise direction, the radiation shield including a shielding body including a sheet-type lower shielding portion made of a radiation shielding material and sheet-type upper shielding portions extending from widthwise opposite ends of the lower shielding portion, respectively, and made of a radiation shielding material; and guide members formed at the widthwise opposite ends of the lower shielding portion on one surface of the lower shielding portion and inserted into the guide grooves of the radiotherapy apparatus, respectively. Therefore, the disclosed radiation shield can demonstrate an excellent radiation shielding effect and is easily manageable during radiotherapy treatment.

9 Claims, 3 Drawing Sheets a—a'

RADIATION SHIELD

BACKGROUND

1. Field

The present invention relates to a radiation shield, which can inhibit non-treatment areas from being exposed to radiation during radiotherapy treatment, and more particularly to a radiation shield, which has an excellent radiation shielding effect and is convenient to use.

2. Description of the Related Art

Although radiation exposure has an extremely harmful effect, radiation is unavoidably employed to accurately diagnose or treat a disease. Therefore, it is necessary to maximally suppress non-treatment areas of a patient's body from being exposed to radiation during radiotherapy treatment, like computed tomography (CT).

In order to inhibit non-treatment areas from being exposed to radiation during radiotherapy treatment, conventionally, medical sheets formed by extrusion after dispersing lead (Pb) components in rubber have been widely used.

Meanwhile, during a CT examination, diagnosis is carried out on a patient while irradiating radiation to treatment areas from all directions over the patient. In this case, however, since the radiation irradiated to non-treatment areas is generally shielded just by covering the patient's treatment areas with a shielding sheet in a state in which the patient lies in a bed, the radiation shielding effect is not so high.

CITATION LIST

Patent Publication (Patent publication 1): KR10-0909075 B1
(Patent publication 2): KR10-1607289 B1

SUMMARY

The present invention has been made in an effort to solve the problems of the prior art, and it is an object of the present invention to provide a radiation shield, which is easily manageable when a radiation shielding operation is performed on a human body.

It is another object of the present invention to provide a radiation shield, which can effectively shield radiation during radiotherapy treatment.

The above objects of the present invention can be accomplished by providing a radiation shield for a radiotherapy apparatus having guide grooves which are formed at widthwise opposite ends of a bed and extend in a lengthwise direction of the bed, the radiation shield including a shielding body including a sheet-type lower shielding portion made of a radiation shielding material and sheet-type upper shielding portions extending from widthwise opposite ends of the lower shielding portion, respectively, and made of a radiation shielding material, and guide members formed at the widthwise opposite ends of the lower shielding portion on one surface of the lower shielding portion and configured to be inserted into the guide grooves of the radiotherapy apparatus, respectively.

The shielding body may include: a radiation shielding agent including one or more of a tin compound, an antimony compound, a barium compound, a tungsten compound, an indium compound and gadolinium compound; and a binder including one or more of natural rubber, synthetic rubber and synthetic resin. Here, the shielding body may include 20 to 30% by weight of the tin compound, 10 to 20% by weight of the antimony compound, 35 to 45% by weight of the barium compound, 1 to 3% by weight of the tungsten compound, 1 to 3% by weight of an indium compound, 1 to 3% by weight of the gadolinium compound, and 10 to 30% by weight of the binder.

The shielding body may include multiple folds of sheet made of a radiation shielding material.

Insertion guides protruding outwardly in a lengthwise direction of the lower shielding portion may be formed at ends of the guide members.

The guide members may be connected to the lower shielding portion by means of spacers defining spacing distances between the guide members and the lower shielding portion and made of a flexible material.

Protection covers may be formed on both surfaces of the shielding body.

A rim protection cover may be formed along a rim of the shielding body.

The shielding body may include a radiation shielding agent including lead (Pb), and a binder including one or more of natural rubber, synthetic rubber and synthetic resin.

As described above, the radiation shield according to the present invention is installed in a radiotherapy apparatus and easily shields a patient from radiation.

In addition, the radiation shield according to the present invention has an excellent radiation shielding effect by shielding a patient from radiation irradiated from all directions over the patient.

When the radiation shield is made of a lead-free material, a risk caused due to lead (Pb) component leaks can be reduced and the weight of the radiation shield can be reduced, thereby easily managing the radiation shield.

DETAILED DESCRIPTION

Hereinafter, a specific embodiment of the present invention will be described in detail with reference to the accompanying drawings.

The present invention relates to a radiation shield which is installed in a radiotherapy apparatus and inhibits non-treatment areas of a patient from being exposed to radiation during radiotherapy treatment.

Figure 1:
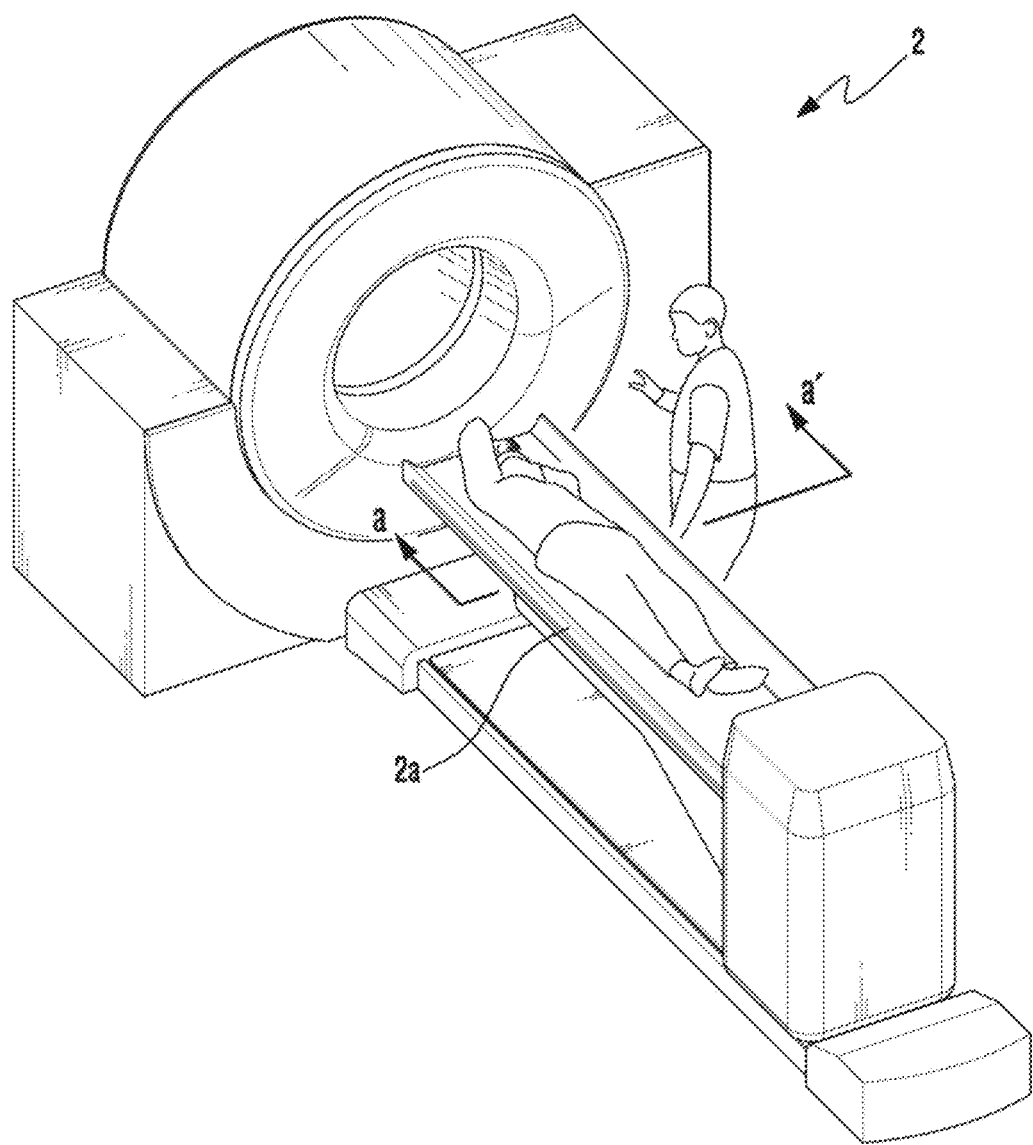
FIG. 1 is a perspective view of a radiotherapy apparatus employing a radiation shield according to the present invention.
Figure 2:
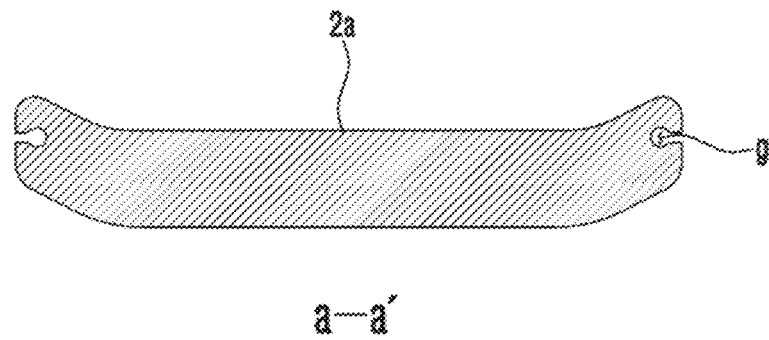
FIG. 2 is a cross-sectional view of a bed portion of the radiotherapy apparatus.

As illustrated in FIGS. 1 and 2, the radiation shield according to the present invention is applied to the radiotherapy apparatus 2 whose a bed 2a includes guide grooves g formed at widthwise opposite ends of the bed 2a, and the guide grooves extend in a lengthwise direction of the bed.

Figure 3:
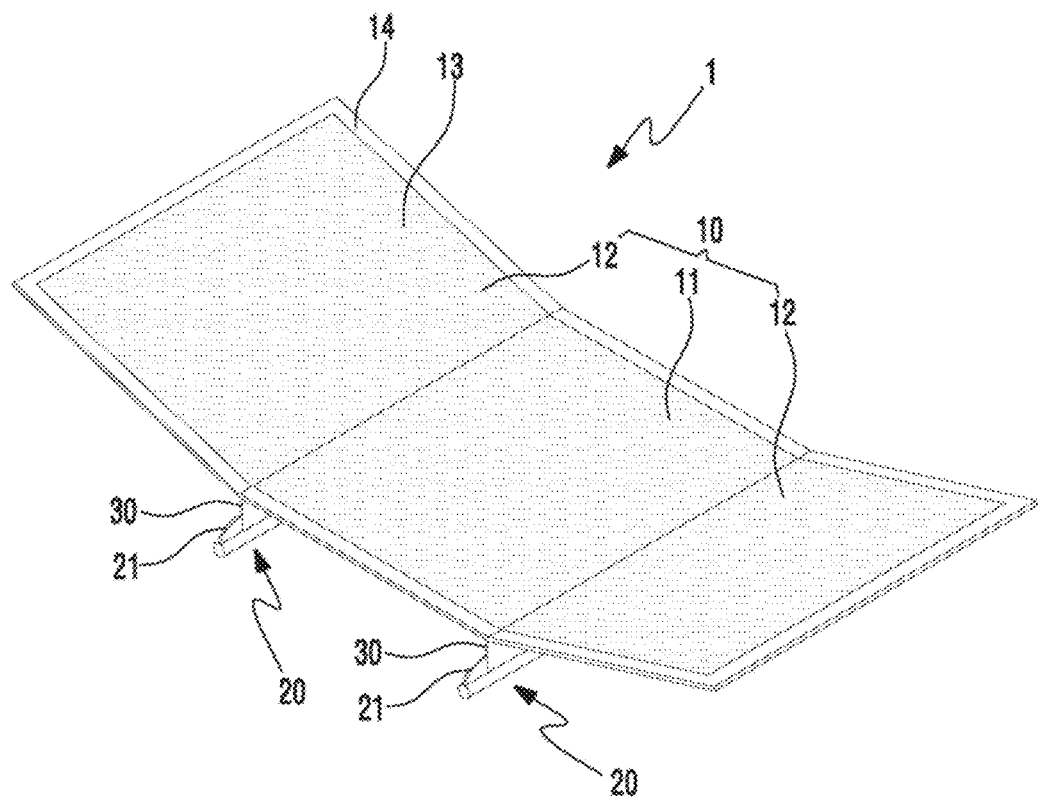
FIG. 3 is a perspective view of a radiation shield according to the present invention.

A perspective view of a radiation shield 1 according to the present invention is illustrated in FIG. 3. The radiation shield 1 according to the present invention includes a shielding body 10, and guide members 20.

The shielding body 10 is formed of a sheet-type member including a radiation shielding material to inhibit the patient's non-treatment areas from being exposed to radiation during radiotherapy treatment using the radiotherapy apparatus by surrounding the non-treatment areas.

Specifically, the shielding body 10 may include a radiation shielding agent including one or more of a tin (Sn) compound, an antimony (Sb) compound, a barium (Ba) compound, a tungsten (W) compound, an indium (In) compound and gadolinium (Gd) compound, and a binder including one or more of natural rubber, synthetic rubber and synthetic resin.

As understood from the terms, the radiation shielding agent, such as a tin (Sn) compound, performs a radiation shielding function, and the binder binds powdery particulates of the radiation shielding agent to maintain a flexible sheet shape.

Barium (Ba) is not harmful to a human body and can effectively shield X-ray radiation, compared to lead (Pb). Tin (Sn) and antimony (Sb) have high low-energy radiation absorption coefficients. Tungsten (W) has a very high radiation shielding rate, and gadolinium (Gd) absorbs neutrons.

As described above, the shielding body 10, including various lead-free elements, can avert a risk caused due to lead (Pb) component leaks and can absorb radiations being in a variety of energy states.

The shielding body 10 preferably includes 20 to 30% by weight of the tin compound, 10 to 20% by weight of the antimony compound, 35 to 45% by weight of the barium compound, 1 to 3% by weight of the tungsten compound, 1 to 3% by weight of the indium compound, 1 to 3% by weight of the gadolinium compound, and 10 to 30% by weight of the binder. Since the shielding body 10 is approximately 10% lighter than a lead-containing radiation shielding sheet, it is easily manageable.

In an example embodiment of the present invention, tin dioxide ($SnO_2$) may be used as the Sn compound, antimony trioxide ($Sb_2O_3$) may be used as the tin compound, barium sulfate ($BaSO_4$) may be used as the barium compound, tungsten dioxide ($WO_2$) may be used as the tungsten compound, indium oxide ($In_2O_3$) may be used as the indium compound, and gadolinium dioxide (II) ($Gd_2O_3$) may be used as the gadolinium compound.

Figure 4:
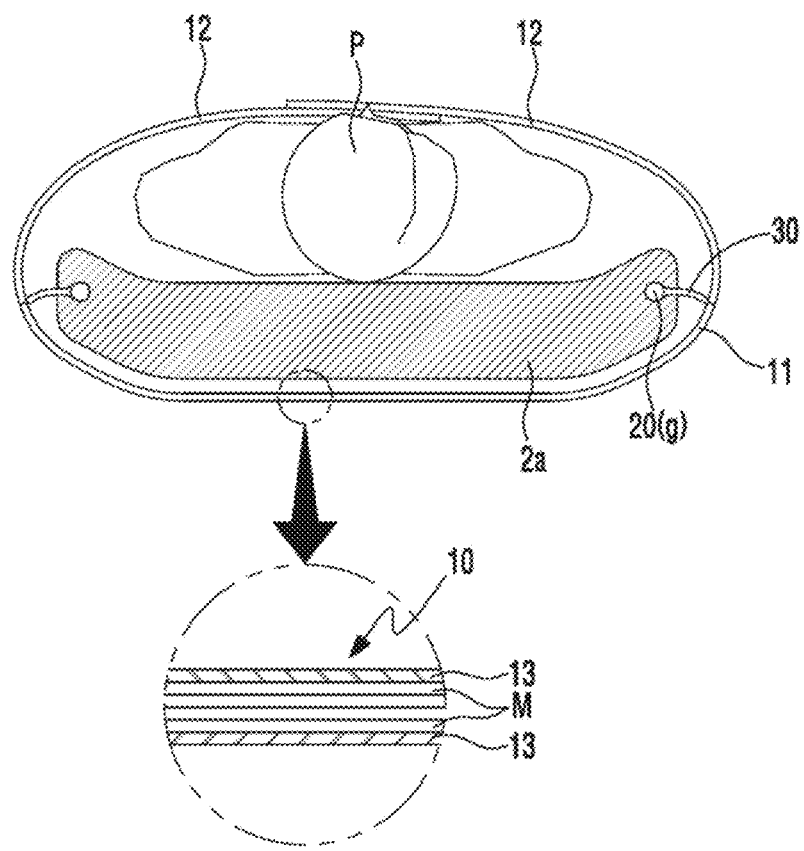
FIG. 4 is a cross-sectional view illustrating a state in which the radiation shield according to the present invention is installed in a radiotherapy apparatus.

The shielding body 10 includes a lower shielding portion 11 and upper shielding portions 12 extending from widthwise opposite ends of the lower shielding portion 11. The lower shielding portion 11 and the upper shielding portions 12 are all made of radiation shielding materials and are formed in sheet types. As illustrated in FIG. 4, the shielding body 10 is installed in the radiotherapy apparatus 2 such that the lower shielding portion 11 is positioned below the bed 2a and the upper shielding portions 12 are positioned above the bed 2a. That is to say, the shielding body 10 is installed so as to surround the bed 2a and a patient P in a state in which the patient P lies in the bed 2a of the radiotherapy apparatus 2, thereby shielding the patient P from radiation irradiated from all directions over the patient P.

Two of the guide members 20 are formed at widthwise opposite ends of the lower shielding portion 11 on one surface of the lower shielding portion 11, respectively, and are inserted into the guide grooves g formed at widthwise opposite ends of the bed 2a of the radiotherapy apparatus 2, respectively. The guide members 20 inserted into the guide grooves g allow the radiation shield according to the present invention 1 to be easily fixed to the radiotherapy apparatus 2 and to move along the guide grooves g of the bed 2a so as to surround the patient's non-treatment areas which are required to be shielded from radiation.

In order to allow the guide members 20 to be easily inserted into the guide grooves g of the radiotherapy apparatus 2, the guide members 20 are preferably made of a rigid material, compared to the shielding body 10, to maintain a constant shape.

The shielding body 10 may be formed of multiple folds of sheet M including a radiation shielding material.

The sheet M, which is relatively thin, is easy to fabricate and handle. In addition, it is possible to form the shielding body 10 so as to have a desired shielding rate by adjusting the number of folds of the sheet M having a certain shielding rate.

Insertion guides 21 protruding outwardly along a lengthwise direction of the lower shielding portion 11 may be formed at ends of the guide members 20.

Since the insertion guides 21 outwardly protruding along the lengthwise direction of the lower shielding portion 11 have no overlapping portions with respect to the shielding body 10 and are easily distinguished from the shielding body 10 by naked eyes, guide members 20 can be easily inserted into the guide grooves g of the radiotherapy apparatus 2 without interference of the shielding body 10.

The guide members 20 are preferably connected to the lower shielding portion 11 by means of spacers 30.

The spacers 30 define spacing distances between the guide members 20 and the lower shielding portion 11 and are made of a flexible material, so that the guide members 20 are allowed to move within the range of a radius which is defined by a width of the spacers 30 with respect to the lower shielding portion 11. Accordingly, the guide members 20 can be easily inserted into the guide grooves g of the radiotherapy apparatus 2. In addition, even if a distance between the guide grooves g of the radiotherapy apparatus 2 is not precisely equal to a distance between the guide members 20, the radiation shield according to the present invention can be applied to the radiotherapy apparatus 2.

Protection covers 13 may be formed on both surfaces of the shielding body 10.

The protection covers 13 are made of for example, synthetic fiber, and covers the flexible shielding body 10, thereby inhibiting the shielding body 10 from being damaged due to repeated use of the radiation shield according to the present invention. Particularly, in a case where the shielding body 10 is formed of multiple folds of thin sheet M, the outermost fold of sheet M can be effectively inhibited from being damaged.

When the protection covers 13 are formed on both surfaces of the shielding body 10, the guide members 20 need to be formed outside the protection covers 13.

A rim protection cover 14 may be formed along the rim of the shielding body 10.

Like the protection covers 13, the rim protection cover 14 can inhibit the shielding body 10 from being damaged due to repeated use of the radiation shield according to the present invention. In addition, when the shielding body 10 is formed of multiple folds of thin sheet M, the rim protection cover 14 is sewed on the rim of the shielding body 10 to integrally form the sheet folds.

According to another example embodiment of the present invention, the shielding body 10 of the radiation shield 1 may include a radiation shielding agent including lead (Pb); and a binder including one or more of natural rubber, synthetic rubber and synthetic resin.

The radiation shielding agent including a lead (Pb) component may perform a radiation shielding function, and the binder may bind powdery particulates of the radiation shielding agent to maintain a flexible sheet shape.

The lead (Pb) component is advantageous in that it exhibits an excellent radiation shielding effect and is inexpensive.

The radiation shield according to the present invention may further include a handle (not shown) or a Velcro (not shown) attached to a side of the shielding body 10 in addition to the aforementioned components. The handle may allow the radiation shield to be easily transported. The Velcro formed at the upper shielding portions 12 may allow the upper shielding portions 12 to be joined to each other, thereby making the radiation shield keep surrounding the patient during radiotherapy treatment.

While the present invention have been particularly shown and described with reference to exemplary embodiments thereof, it will be understood by those of ordinary skill in the art that various changes in form and details may be made therein without departing from the spirit and scope of the present invention as defined by the following claims.

| Explanation of reference numerals | |
|---|---|
| 1: Radiation shield | 2: Radiotherapy apparatus |
| 2a: Bed | 10: Shielding body |
| 11: Lower shielding portion | 12: Upper shielding portions |
| 13: Protection covers | 14: Rim protection cover |
| 20: Guide members | 21: Insertion guides |
| 30: Spacers | g: Guide grooves |
| M: Sheet | |

What is claimed is:

1. A radiation shield for a radiotherapy apparatus having guide grooves which are formed at widthwise opposite ends of a bed and extend in a lengthwise direction of the bed, the radiation shield comprising:
    a shielding body including a sheet-type lower shielding portion made of a radiation shielding material and sheet-type upper shielding portions extending from widthwise opposite ends of the lower shielding portion, respectively, and made of a radiation shielding material; and
    guide members formed at the widthwise opposite ends of the lower shielding portion on one surface of the lower shielding portion and configured to be inserted into the guide grooves of the radiotherapy apparatus, respectively.

2. The radiation shield of claim 1, wherein the shielding body comprises: a radiation shielding agent including one or more of a tin compound, an antimony compound, a barium compound, a tungsten compound, an indium compound and gadolinium compound; and a binder including one or more of natural rubber, synthetic rubber and synthetic resin.

3. The radiation shield of claim 2, wherein the shielding body comprises 20 to 30% by weight of the tin compound, 10 to 20% by weight of the antimony compound, 35 to 45% by weight of the barium compound, 1 to 3% by weight of the tungsten compound, 1 to 3% by weight of an indium compound, 1 to 3% by weight of the gadolinium compound, and 10 to 30% by weight of the binder.

4. The radiation shield of claim 1, wherein the shielding body includes multiple folds of sheet made of a radiation shielding material.

5. The radiation shield of claim 1, wherein insertion guides protruding outwardly in a lengthwise direction of the lower shielding portion are formed at ends of the guide members.

6. The radiation shield of claim 1, wherein the guide members are connected to the lower shielding portion by means of spacers defining spacing distances between the guide members and the lower shielding portion and made of a flexible material.

7. The radiation shield of claim 1, wherein protection covers are formed on both surfaces of the shielding body.

8. The radiation shield of claim 1, wherein a rim protection cover is formed along a rim of the shielding body.

9. The radiation shield of claim 1, wherein the shielding body comprises:
    a radiation shielding agent including lead (Pb); and
    a binder made of one or more of natural rubber, synthetic rubber and synthetic resin.

* * * * *